United States Patent [19]
Greenwood et al.

[11] Patent Number: 5,004,455
[45] Date of Patent: Apr. 2, 1991

[54] INFECTION-RESISTANT CATHETER

[76] Inventors: Eugene C. Greenwood, 2956-B Pepper Tree La., Costa Mesa, Calif. 92626; John Hyatt, 7 Jade Cove, Corona Del Mar, Calif. 92625

[21] Appl. No.: 380,526

[22] Filed: Jul. 17, 1989

[51] Int. Cl.$^5$ .............................................. A61M 3/00
[52] U.S. Cl. ...................................... 604/43; 604/264; 604/280
[58] Field of Search ................... 604/264, 280, 43, 39, 604/27, 19

[56] References Cited

U.S. PATENT DOCUMENTS 4,717,379 1/1988 Ekholmer ........................... 604/280
4,867,742 9/1989 Calderon ....................... 604/121 X Primary Examiner—John D. Yasko

[57] ABSTRACT

A draining catheter for the prevention of infectious diseases around its outside periphery, which has a secondary channel system for the application of antimicrobial agents to the area surrounding its outside periphery.

3 Claims, 1 Drawing Sheet

INFECTION-RESISTANT CATHETER

FIELD OF THE INVENTION

This invention relates to catheters in general and specifically to those for site drainage of the human body. Provision is made to prevent infection.

BACKGROUND OF THE INVENTION

It has long been a method of draining fluids from the human body to insert a flexible, hollow tube into the area where fluid needs draining, for the purpose of providing a pathway for the fluid to exit from the body. These tubes are called catheters.

In the pursuit of this objective, many variations of catheters have been designed. Although they are widely used today, one of the major problems associated with catheters is that they often provide an environment for infections to grow. The most common site is the urinary tract, where 40 percent of all hospital-acquired infections occur. The most common cause of these infections is urethral instrumentation, primarily catheterization. In fact, between 10 and 15 percent of all hospitalized patients have indwelling catheters.

Many methods have been used to fight this problem, flooding of the area with antibiotics and antiseptic solutions prior to the introduction of the catheter, use of a closed-catheter drainage system, periodic instillations of chemicals such as hydrogen peroxide or glutaraldehyde into the collecting bag can delay the onset of bacteriuria, but no devices have been completely effective in eliminating infections in the patient with a long-term indwelling catheter.

Prior art which has addressed this problem is:

U.S. Pat. No. 4,392,848 issued 04-12-83 to Lucas et al entitled CATHETERIZATION; PREVENTING INFECTION comprising a catheter manufactured from a permeable polymer and a lumen through which flows an aqueous solution containing carbolic acid in a reservoir which diffuses through the polymer providing a zone of microbial inhibition around the catheter.

U.S. Pat. No. 4,723,946 issued 02-09-88 to Dennis entitled URINARY CATHETER, HYGIENE SYSTEM AND PROCESS THEREFORE comprising a urinary catheter and cleansing process for cleansing the catheter while in place within the users bladder.

U.S. Pat. No. 4,765,439 issued 01-03-89 to Guest entitled SPIRAL MULTI LUMEN CATHETER comprising a multi-lumen catheter having lumens which do not extend in a straight line down the length of the catheter and method of manufacturing same.

While the foregoing prior art devices provide some protection against infection in the area of catheters, they are clearly ineffective and costly to manufacture. In addition, due to their specificity, some of the prior art is limited in its ability to utilize all of the many anti-microbial solutions which are presently available.

Therefore, there remains a need in the art for a convenient, simple to use, inexpensive to manufacture anti-infection catheter which is effective in combating this consequence of other medical treatments.

SUMMARY OF THE INVENTION

Campbell's UROLOGY, published by W. B. Saunders Company, Chapter 8, *Diagnostic and Therapeutic Urologic Instrumentation*, by Paul H. Lange, M.D., a recognized authority, states the following on the subject of catheter-associated infection: "These catheter-associated infections cause significant morbidity...similarly, 46 percent of adult gram-negative bacteremias were from urinary tract infections or prior genitourinary manipulation. Other infectious complications associated with urethral catheterization and concomitant urinary infections are acute epididymitis-orchitis, bacterial prostatitis, pyelonephritis, periurethral abscesses, struvite bladder and especially renal, calculi."

The prevalence of infections which result from the use of indwelling catheters is found in a definition in Taber's Cyclopedic Medical Dictionary: "Catheter Fever: Reactionary rise in temperature caused by a urinary tract infection following passage of a catheter or urethral bougie."

From all of our investigations, it appears that no one had addressed the treatment of surrounding the catheter with antibiotic creams, anti-microbial agents and/or disinfectants other than Lucas et al in U.S. Pat. No. 4,392,848 wherein any treating solution would have to pass through a permeable wall, necessarily eliminating all fluids containing particulates which would immediately plug the pores. This eliminates all antibiotics, as far as we know.

The present invention solves the problems with a technically sophisticated flow system which permits the application of any medication prescribed.

OBJECTS AND ADVANTAGES

Several objects and advantages of the present invention Infection-Resistant Catheter are:

1. Medicinal and/or analgesic solutions are applied to wherever the catheter is in contact with the body; this offers the advantage of presenting a hostile field to any infectious bacteria which may be present, killing the bacteria before they can spread.

2. A further object of the present invention Infection-Resistant Catheter is to allow frequent changing and renewing of the medicines without removing the catheter, thus always presenting fresh and effective antibiotics, analgesics, disinfectants, etc. to the endangered areas.

3. Another object and advantage of the present invention Infection-Resistant Catheter is the control of the application of the medicines in a manner which will reach all areas; this avoids the danger of leaving untreated "hot spots" for the start of infections.

4. It is a further object to make the treatment easy to administer by semi-skilled personnel, freeing the highly skilled nurse for other duties.

5. It is a further object of the present invention to make the device rugged and practical, thus reducing the danger of failure of the device.

6. It is a further object of the present invention Infection-Resistant Catheter to allow all manipulations of the catheter to take place at a distance away from the catheter's exit from the body, so that no fingers or other potentially infectious items need come in contact with the threatened area.

SUMMARY OF THE INVENTION

It is the general object of the present invention to prevent or greatly reduce infections caused by catheters. This is accomplished by having one or more tubular channels formed as an integral part of the catheter and running parallel to the main drain channel. These are medicating channels which are interconnected into a single channel at a location on the catheter after it exits from the body. This single channel can be connected to a hypodermic syringe through which antibiotic or other anti-microbial agents can then be pumped into the medicating channels. The medicating channels have a series of exit ports through which the anti-microbial agent flows out and into the area surrounding the catheter, preventing infections from growing there.

DESCRIPTION OF THE DRAWINGS

The features of the present invention, which are believed to be novel, are set forth with particularity in the appended claims. The advantages thereof may best be understood by reference to the following description taken in conjunction with the accompanying drawings, in the several figures of which like reference numerals identify like elements and in which:

FIG. 5 sets forth a section view of an alternate embodiment of the present invention;

FIG. 6 sets forth a partial section side view of FIG. 5 showing a fabric sleeve surrounding the outside diameter of the catheter.

DESCRIPTION OF THE PREFERRED EMBODIMENT

REFERENCE NUMERALS

10 CATHETER
11 CATHETER OUTSIDE DIAMETER
12 COLLECTOR FITTING
14 DRAIN PORT
16 CATHETER END
18 CHECK VALVE
19 HYPO SYRINGE CONNECTION
20 HYPO SYRINGE
22 OUTLET PORT
24 MEDICATING CHANNELS
26 DRAIN COLLECTOR
28 DRAIN PASSAGE
30 DRAIN HEAD

Figure 1:
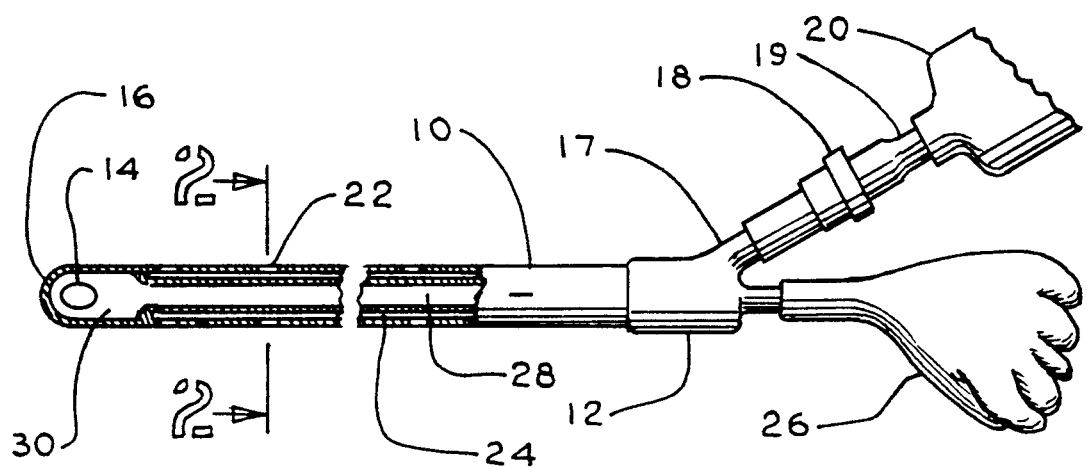
FIG. 1 sets forth a partial section view of an infection-resistant catheter constructed in accordance with the present invention.

FIG. 1 sets forth a partial section view of a catheter constructed in accordance with the present invention and referenced by numeral 10. Catheter 10 includes an elastic tube beginning at rounded end 16 of drain head 30 and ending in two divided sections at the opposite end, one of the sections branching off from collector fitting 12 and progressing through check valve 18, hypodermic syringe connection 19 to hypodermic syringe 20, which is removable; the other section terminates in flexible container 26 for receiving the fluid being drained.

Proximate rounded end 16 of drain head 30 is an entrance hole 14 through which the fluid to be drained can enter and flow through main channel 28, ending in flexible container 26. In some cases, flexible container 26 is replaced by a long tube which ends in a conveniently placed open container.

Molded into the wall of the catheter parallel to the main channel are four secondary medicating channels 24a, 24b, 24c and 24d which extend from drain head 30, where they are closed and sealed, to collector fitting 12 wherein they are all joined and feed into fitting outlet 17. This flow line now passes through check valve 18 and hypodermic syringe connection 19 to hypodermic syringe 20.

At three-eights inch spacing or thereabout spacing along each medicating channel 24a, 24b, 24c, and 24d are slits 22, which are made with a sharp piercing blade from the outside diameter 11 of catheter 10 through into medicating channels 24a, 24b, 24c and 24d. No material is removed from catheter 10 in making slit 22, causing slit 22 to close up when the blade is withdrawn after cutting the slit. Slits 22 are 0.06 or thereabout in length, their actual length being dependent upon the thickness of the wall from the outside diameter 22 to the closest wall of channel 24 and the durometer of the elastomeric material selected for the catheter. The determining factor is the pressure required in channels 24 provided by hypodermic syringe 20 to force the slit to open and release the anti-microbial agent to outside of catheter 10. By providing this pressurized system, it is assured that all slits will open simultaneously and release the injected anti-microbial agent when hit with a pressure of more than that required to open the shortest slit. Collector fitting 12 is sealingly attached to catheter 10 by adhesion or other method, which will not leak under the pressure of the fluid being pumped by the hypodermic syringe.

Catheter 10 is preferably constructed of a biocompatible polymer such as latex, polyvinyl chloride, polyurethane or silicone.

Figure 2:
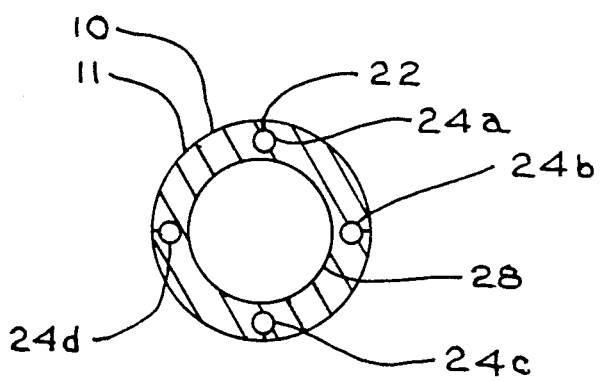
FIG. 2 sets forth a section view taken along section line 2—2 of FIG. 1.

FIG. 2 sets forth an enlarged cross section view of catheter 10 showing four medicinal channels 24a, 24b, 24c and 24d and slits 22 passing from catheter outside diameter 22 through to channels 24a, b, c, and d. Main channel 28 is shown passing through the center of catheter 10.

Figure 4:
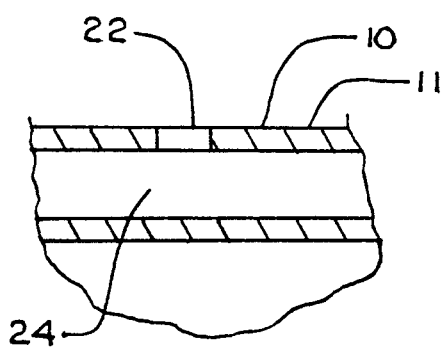
FIG. 4 sets forth a section view taken along section line 4—4 of FIG. 3.
Figure 3:
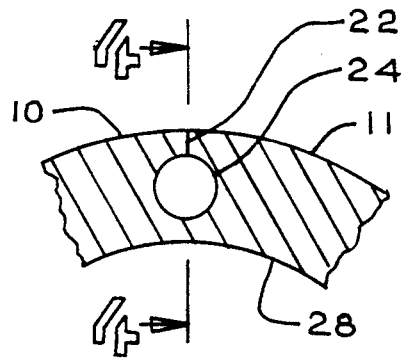
FIG. 3 sets forth an enlarged section view of the catheter at the location of one of the medicating channels.

FIGS. 3 and 4 show further enlarged views of secondary medicinal channel 24a and slit 22.

OPERATION OF THE INVENTION

Typical of the operation of the present invention Infection-Resistant Catheter is its use as a ureteral catheter. In this usage, the catheter is inserted through the urethra and into the bladder in order to control the outflow of urine from the bladder. For this purpose a material is selected which is a compromise—it must be as soft as possible while still retaining enough stiffness to allow its insertion by compression against the resistance of the wall of the urethra. The outside diameter is 14F, a standard catheter designation. Each F unit is 0.33 mm, therefore the diameter is 4.62 mm or 0.18 inches.

After the catheter is in place with the catheter head inside the bladder and the drain outlet attached to an empty flexible container, a hypodermic syringe with the prescribed anti-microbial agent in its barrel is attached to the hypodermic connection and the syringe's piston driver is pressed firmly and swiftly to the completely closed position, ejecting the anti-microbial agent into the secondary channels of the catheter. The collector fitting directs the agent to all secondary medicating channels simultaneously. The pressure exerted on the fluid by the syringe opens all slits simultaneously and flows the medicine outward and into the area between the urethra and the catheter outside diameter.

A certain amount of the medicine will remain within the medicinal channels and is contained therein by the check valve located in front of the hypodermic syringe. After ejecting the medicine, the hypodermic syringe is removed. At regularly scheduled intervals, more anti-microbial fluid may be added or another medicine introduced.

CONCLUSION, RAMIFICATIONS AND SCOPE OF INVENTION

Thus, the reader will see that the present invention provides a highly reliable, economical device which addresses a serious problem in health science . This basic improvement in catheters can result in prolonged life and reduced suffering for large numbers of ill people. With the continuous discovery of improved antibiotics the present invention provides a way of utilizing these medicines to their best advantage.

While our description above contains many specific details, these should not be construed as limitations on the scope of the invention, but rather as an example of one of the many variations which are possible. For example, the slits indicated in the preferred embodiment may be replaced by needle punctures in which no material is removed but which provide a very small fluid passage when put under pressure. A balloon may be provided for catheter anchorage. The number of medicating channels may be reduced to as few as one or increased to more than four. Anti-microbial, of course, includes anti-fungal and anti-viral activity as well. New discoveries in plastics may provide materials which are better suited to the application than those listed. While the embodiments described are typical of ureter catheters, the present invention can be adapted for use in wound drainage, transtrachial oxygen delivery, and other catheter requirements, Accordingly, the scope of the invention should be determined not by the embodiments illustrated, but by the appended claims and their legal equivalents.

That which is claimed:

1. A catheter comprising:
   an elastomeric tubular device for passing into the human body containing
   a first channel passing through the entire length of said catheter, open proximate one end to the outside of said catheter for receiving fluid, and a means at the other end to contain or dispose of said fluid, and
   one or more secondary channels generally parallel to said first channel with closed ends proximate the open end of said first channel, with slits or punctures through the wall to the periphery of said catheter, said slits or punctures being dimensionless and closed by elastic memory until pressurized from within said secondary channel or channels.

2. A catheter as set forth in claim 1 wherein said secondary channels are combined into one channel proximate the open end.

3. A catheter as set forth in claim 1 wherein said combined channel contains connecting means for connecting to a pressure and pumping source.

* * * * *